(12) United States Patent
Suzuki et al.

(10) Patent No.: US 10,252,324 B2
(45) Date of Patent: Apr. 9, 2019

(54) MOLD RELEASE AGENT COMPOSITION FOR USE IN CASTING

(71) Applicant: YUSHIRO CHEMICAL INDUSTRY CO., LTD., Ota-ku (JP)

(72) Inventors: Mikinori Suzuki, Koza-gun (JP); Yasuhiro Hattori, Koza-gun (JP); Tamotsu Matsuki, Koza-gun (JP); Midori Nakazato, Koza-gun (JP); Yasunari Oshimoto, Koza-gun (JP)

(73) Assignee: YUSHIRO CHEMICAL INDUSTRY CO., LTD., Ota-ku (JP)

( * ) Notice: Subject to any disclaimer, the term of this patent is extended or adjusted under 35 U.S.C. 154(b) by 0 days.

(21) Appl. No.: 15/568,075

(22) PCT Filed: Jun. 24, 2016

(86) PCT No.: PCT/JP2016/068900
§ 371 (c)(1),
(2) Date: Oct. 20, 2017

(87) PCT Pub. No.: WO2016/208743
PCT Pub. Date: Dec. 29, 2016

(65) Prior Publication Data
US 2018/0117667 A1    May 3, 2018

(30) Foreign Application Priority Data

Jun. 26, 2015    (JP) .................. 2015-129173

(51) Int. Cl.
| | |
|---|---|
| B22C 3/00 | (2006.01) |
| C08L 83/04 | (2006.01) |
| B22D 17/20 | (2006.01) |
| C07C 15/44 | (2006.01) |
| C08K 5/01 | (2006.01) |
| C08K 5/56 | (2006.01) |
| C08G 77/00 | (2006.01) |

(52) U.S. Cl.
CPC .............. B22C 3/00 (2013.01); B22D 17/20 (2013.01); C07C 15/44 (2013.01); C08G 77/80 (2013.01); C08K 5/01 (2013.01); C08K 5/56 (2013.01); C08L 83/04 (2013.01)

(58) Field of Classification Search
CPC .... B22C 3/00; C08K 5/01; C08K 5/56; C08L 83/04; C07C 15/44; B22D 17/20
See application file for complete search history.

(56) References Cited

U.S. PATENT DOCUMENTS

| | | | |
|---|---|---|---|
| 2007/0131140 A1 | 6/2007 | Aoki et al. | |
| 2011/0034357 A1* | 2/2011 | Kawata | ............... C10M 169/04 508/202 |

FOREIGN PATENT DOCUMENTS

| | | |
|---|---|---|
| CN | 101010156 A | 8/2007 |
| CN | 102585233 A | 7/2012 |
| JP | 2007-326145 A | 12/2007 |
| JP | 2011-056518 A | 3/2011 |
| JP | 2011-161464 A | 8/2011 |
| WO | 2006/025368 A1 | 3/2006 |
| WO | 2013/121851 A1 | 8/2013 |
| WO | WO 2013/122238 A1 | 8/2013 |
| WO | WO-2013121851 A1 * 8/2013 ............... B22C 3/00 |

OTHER PUBLICATIONS

Notification of Reasons for Refusal dated Mar. 3, 2017, in Japanese Patent Application No. 2016-574484 filed Jun. 24, 2016 (with English translation).
Combined Office Action and Search Report dated May 14, 2018 in Chinese Patent Application No. 201680027990.5, (with English translation of categories of cited documents), citing documents AO-AQ therein, 7 pages.
Office Action dated Sep. 25, 2018, in Chinese Patent Application No. 201680027990.5 (w/ Computer-generated English translation).

\* cited by examiner

*Primary Examiner* — Taiwo Oladapo
(74) *Attorney, Agent, or Firm* — Oblon, McClelland, Maier & Neustadt, L.L.P.

(57) ABSTRACT

The present invention provides a novel mold release agent composition which can cope with a higher temperature range than that of the conventional mold release agent composition. That is, a mold release agent composition for use in casting of the present invention contains a silicone oil and a solvent, wherein the silicone oil contains 30% by mass or more of a first silicone oil represented by the formula (1) and 70% by mass or less of a second silicone oil represented by the formula (2), with respect to the total amount of the silicone oil. In the formula (1), $R^1$ is an alkyl group having 1 to 6 carbon atoms; and $R^2$ is an aralkyl group, a phenyl group, or a mercaptoalkyl group. In the formula (2), $R^3$ is an alkyl group having 8 or more carbon atoms; and $R^4$ is an aralkyl group, a phenyl group, or a mercaptoalkyl group.

16 Claims, 4 Drawing Sheets

MOLD RELEASE AGENT COMPOSITION FOR USE IN CASTING

TECHNICAL FIELD

The present invention relates to a mold release agent composition for use in casting. More specifically, the present invention relates to a mold release agent composition for use in casting which is used in a state where it is applied to a mold of a casting machine.

BACKGROUND ART

In casting, a mold release agent is applied to the surface of a mold for the purpose of suppressing welding between the mold and a product to improve mold release. Conventionally, many aqueous dilution type mold release agents have been used as the mold release agent. The mold release agent contains 95% or more of water, and a small content of an active ingredient exhibiting a mold release action. The aqueous dilution type mold release agent is used in a method of spraying a large amount of the mold release agent onto the mold to cool the mold, applying the large amount of the mold release agent to secure the necessary amount of the active ingredient, and forming a coated film on the surface of the mold. However, this use method has a problem that the amount of waste of the aqueous dilution type mold release agent is extremely increased.

On the other hand, in recent years, with an improvement in the internal cooling technique of a mold, the use of an oily mold release agent has been started. Since the oily mold release agent can provide an effect in a use amount much smaller than that of the aqueous dilution type mold release agent, the oily mold release agent has no problem of a waste treatment, which is a large advantage. Furthermore, since the mold is not quenched for each shot as with the aqueous dilution type mold release agent, the use of the oily mold release agent has also been confirmed to allow the life of the mold to be lengthened as an advantage. The following Patent Literatures 1 and 2 have been known as such an oily mold release agent.

CITATIONS LIST

Patent Literatures

Patent Literature 1: International Publication No. 2006/025368

Patent Literature 2: Japanese Unexamined Patent Publication No. 2011-161464

SUMMARY OF INVENTION

Technical Problems

As described above, the oily mold release agent exhibits excellent effects. But on the other hand, since the oily mold release agent hardly has a cooling action on the mold, the temperature increase of the mold due to the use thereof cannot be suppressed in some cases even if the internal cooling of the mold is strengthened in casting of large parts or the like. In such a case, the application of the oily mold release agent causes problems such as solidification or baking of the oily mold release agent, and inability to form a mold release coated film from the occurrence of a Leidenfrost phenomenon. Therefore, a case where the mold must be cooled using external cold water to a temperature at which no baking occurs and a temperature at which no Leidenfrost phenomenon occurs, or a case where the conventional aqueous dilution type mold release agent must be used in combination occur. The application range of the oily mold release agent is limited under present circumstances.

The above Patent Literature 1 is an excellent technique showing a basic form as the oily mold release agent. However, the internal cooling as described above cannot catch up. The oily mold release agent has not yet exhibited sufficient performance capable of corresponding to the case where the temperature of the mold is increased. That is, since the oily mold release agent of Patent Literature 1 may cause the solidification or baking of the mold release agent at high temperature, or may make it difficult to form the mold release coated film, the oily mold release agent is required to cope with a wider temperature range.

The above Patent Literature 2 attempts to cope with the baking and the Leidenfrost phenomenon by using a high-viscosity mineral oil in view of the problem of the above Patent Literature 1. However, since the use amount of the high-viscosity mineral oil is increased, the viscosity of the oily mold release agent is increased, which causes a problem that the oily mold release agent is easily affected by ambient temperature. If the influence of the temperature is increased, it is feared that injection becomes unstable during applying. Since the temperature of the surface of the mold is not uniform, it is feared that the mineral oil remains at low temperature. This is because the residual of the mineral oil causes problems such as discoloration of the product and deterioration in the performance of the mold release coated film.

The present invention has been made in view of the above circumstances, and an object of the present invention is to provide a novel mold release agent composition which can correspond to a higher temperature range than that of a conventional mold release agent composition.

Solutions to Problems

The present inventors have found that a silicone oil having an alkyl group having 4 or less carbon atoms in a dialkylsiloxane unit is blended in an amount of 30% by mass or more with respect to the total amount of the silicone oil, and a silicone oil having an alkyl group having 6 or more carbon atoms in a dialkylsiloxane unit is blended in an amount of 70% by mass or less with respect to the total amount of the silicone oil, thereby achieving a high mold release action without causing solidification or baking even in a high-temperature mold, thus completing the present invention.

Furthermore, the present inventors have found that the blending ratio of the silicone oil in the mold release agent composition for use in casting can be increased by using the silicone oil containing the specific dialkylsiloxane unit. The present inventors have found a phenomenon in which a Leidenfrost temperature is rather increased by an increase in the blending ratio without causing solidification or baking even if the blending ratio of the silicone oil is increased. That is, the present inventors have found that the Leidenfrost temperature can be increased while the use of an oil component having a large viscosity variation due to a temperature is suppressed. And, the present inventors have found that this suppresses the influence of temperature to allow a homogeneous mold release coated film to be formed in a wider temperature range.

That is, the present invention is as follows.

<1> A mold release agent composition for use in casting according to claim 1 contains a silicone oil and a solvent, wherein: the silicone oil contains at least a first silicone oil represented by the following formula (1), or the first silicone oil and a second silicone oil represented by the following formula (2); and an amount of the first silicone oil is 30% by mass or more and an amount of the second silicone oil is 70% by mass or less, with respect to the total amount of the silicone oil,

[Chemical Formula 1]

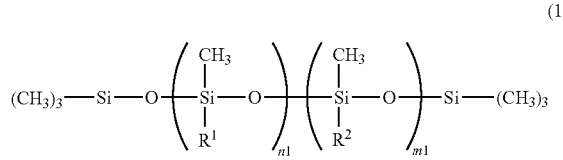

(1)

wherein: $R^1$ is an alkyl group having 1 to 4 carbon atoms; $R^2$ is selected from the group consisting of an aralkyl group, a phenyl group, and a mercaptoalkyl group; n1 is a positive integer; and m1 is 0 or a positive integer,

[Chemical Formula 2]

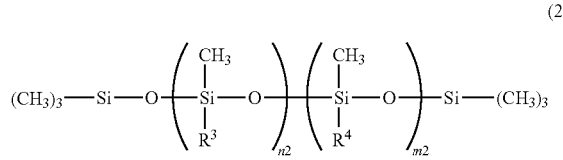

(2)

wherein: $R^3$ is an alkyl group having 6 or more carbon atoms; $R^4$ is selected from the group consisting of an aralkyl group, a phenyl group, and a mercaptoalkyl group; n2 is a positive integer; and m2 is 0 or a positive integer.

<2> The mold release agent composition for use in casting according to claim 1, wherein, when the total amount of the silicone oil and the solvent is taken as 100% by mass, an amount of the silicone oil is 15% by mass or more.

<3> The mold release agent composition for use in casting according to claim 1 or 2, wherein, when a total amount of the mold release agent composition for use in casting is taken as 100% by mass, an amount of the solvent is 55% by mass or more.

<4> The mold release agent composition for use in casting according to any one of claims 1 to 3, wherein the mold release agent composition for use in casting contains a mineral oil and/or a synthetic oil.

<5> The mold release agent composition for use in casting according to any one of claims 1 to 4, wherein the mold release agent composition for use in casting contains a radical capture agent.

<6> The mold release agent composition for use in casting according to claim 5, wherein, when the total amount of the silicone oil is taken as 100 parts by mass, a blended amount of the radical capture agent is 1 part by mass or more.

<7> The mold release agent composition for use in casting according to claim 5 or 6, wherein the mold release agent composition for use in casting contains an organometallic compound as an auxiliary agent for the radical capture agent.

Advantageous Effects of Invention

In the mold release agent composition for use in casting according to claim 1, the content of the first silicone oil in which the number of carbon atoms of each of two alkyl groups in a dialkylsiloxane unit is 1 or more and 4 or less is 30% by mass or more of the total amount of the silicone oil, and the content of the second silicone oil in which the number of carbon atoms of at least one of two alkyl groups in the dialkylsiloxane unit is 6 or more is 70% by mass or less of the total amount of the silicone oil. This constitution makes it possible to prevent the solidification of the mold release agent composition for use in casting even on the surface of a high-temperature mold to maintain the fluidity thereof, and makes it possible to exhibit a mold release action in a higher temperature range than that of a conventional mold release agent composition.

In the mold release agent composition for use in casting according to claim 2, when the total amount of the silicone oil and the solvent is taken as 100% by mass, an amount of the silicone oil is 15% by mass or more. This constitution makes it possible to provide a high Leidenfrost temperature to prevent a Leidenfrost phenomenon on the surface of a mold at high temperature. This makes it possible to exhibit a mold release action in a higher temperature range that that of the conventional mold release agent composition.

In the mold release agent composition for use in casting according to claim 3, an amount of the solvent is 55% by mass or more with respect to the total amount of the composition. This constitution makes it possible to suppress an increase in a viscosity to suppress the influence of ambient temperature on an application amount.

The mold release agent composition for use in casting according to claim 4 contains a mineral oil and/or a synthetic oil. This constitution makes it possible to secure the uniformity of the formed coated film.

The mold release agent composition for use in casting according to claim 5 contains a radical capture agent. This constitution makes it possible to prevent the solidification of the first silicone oil to more certainly maintain the fluidity when the number of carbon atoms of the alkyl group in the dialkylsiloxane unit in the first silicone oil is large within a range of 4 or less.

The mold release agent composition for use in casting according to claim 7 contains an organometallic compound as an auxiliary agent for the radical capture agent. This constitution allows the fluidity of the coated film to be ensured for a longer time.

DESCRIPTION OF EMBODIMENTS

Figure 1:
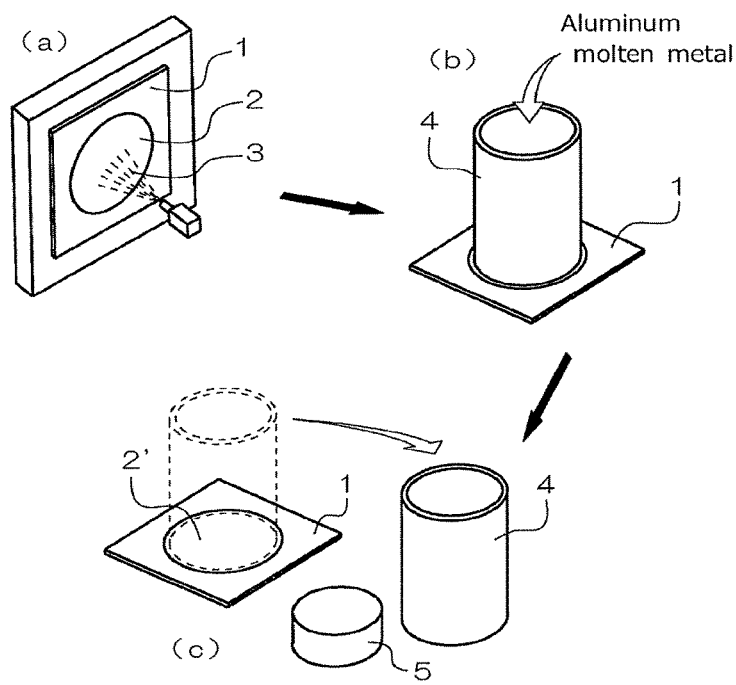
FIG. 1 is an explanatory diagram illustrating a method for evaluating the state of a coated film in Examples.

Hereinafter, the present invention will be described in detail.

A mold release agent composition for use in casting of the present invention contains a silicone oil. The silicone oil is a polymer having a siloxane bond (—Si—O—Si—) as a main chain, and is usually in a liquid state at room temperature (25° C.). The mold release agent composition for use in casting of the present invention contains, as the silicone oil, at least a first silicone oil represented by the formula (1) (hereinafter also simply referred to as a "first silicone oil"), or the first silicone oil and a second silicone oil represented by the formula (2) (hereinafter also simply referred to as a "second silicone oil"). That is, the silicone oil contained in the mold release agent composition for use in casting of the present invention may be only the first silicone oil, or both the first silicone oil and the second silicone oil.

The amount of the first silicone oil is 30% by mass or more, and the amount of the second silicone oil is 70% by mass or less, with respect to the total amount of the silicone oil.

The first silicone oil (hereinafter also simply referred to as a "first silicone oil") is represented by the following formula (1),

[Chemical Formula 3]

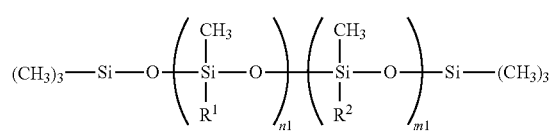

wherein: $R^1$ is an alkyl group having 1 to 4 carbon atoms; $R^2$ is selected from the group consisting of an aralkyl group, a phenyl group, and a mercaptoalkyl group; n1 is a positive integer; and m1 is 0 or a positive integer.

Examples of the alkyl group having 1 to 4 carbon atoms in $R^1$ in the formula (1) include a methyl group, an ethyl group, a propyl group (a n-propyl group, an isopropyl group), and a butyl group (a n-butyl group, a sec-butyl group, an isobutyl group, a tert-butyl group).

The aralkyl group in $R^2$ in the formula (1) represents a group in which an aryl group has an alkyl group as a substituent. The number of carbon atoms of the aryl group constituting the aralkyl group is usually 6 to 14; the number of carbon atoms of the alkyl group constituting the aralkyl group is usually 1 to 12; and the number of carbon atoms of the total of the aralkyl group is usually 7 to 26.

Specific examples of the aryl group constituting the aralkyl group include a phenyl group and a naphthyl group. Examples of the alkyl group constituting the aralkyl group include a heptyl group, an octyl group, a nonyl group, a decyl group, an undecyl group, and a dodecyl group in addition to the various alkyl groups described above as $R^1$. That is, examples of the aralkyl group include a benzyl group, a methylbenzyl group, a tolyl group, a xylyl group, a phenylethyl group, a phenylpropyl group, and a dodecylphenyl group.

Furthermore, the mercaptoalkyl group in $R^2$ represents a group in which the alkyl group has a mercapto group (—SH) as a substituent. The alkyl group constituting the mercaptoalkyl group usually has 1 to 12 carbon atoms. That is, examples of the mercaptoalkyl group include a mercaptomethyl group, a mercaptopropyl group, a mercaptohexyl group, and a mercaptodecyl group.

At least one of hydrogen atoms constituting the alkyl group as $R^1$, and the aralkyl group, the phenyl group, and the mercaptoalkyl group as $R^2$ may be substituted with a halogen atom. Examples of the halogen atom include a fluorine atom and a chlorine atom.

The first silicone oil is contained in an amount of 30% by mass or more (may be 100% by mass) with respect to the total amount of the silicone oil. When the ratio of the first silicone oil to the total of the silicone oil is less than 30% by mass, heat resistance becomes poor, and baking tends to be caused, which is not preferable. The ratio of the first silicone oil to the total of the silicone oil is preferably 40% by mass or more, more preferably 50% by mass or more, and still more preferably 60% by mass or more.

In particular, as a mold temperature is higher, an alkyl group having a smaller number of carbon atoms is preferably selected as $R^1$ in the formula (1), and the ratio of the first silicone oil to the silicone oil is more preferably increased. This makes it possible to maintain fluidity while preventing solidification and baking even in a high-temperature mold.

Although n1 in the formula (1) is not limited, for example, $1 \leq n1 \leq 3000$ can be set. Although m1 in the formula (1) is not limited, for example, $0 \leq m1 \leq 3000$ can be set. Although the correlation between n1 and m1 is not particularly limited, for example, $10 \leq (n1+m1) \leq 3000$ can be set.

The second silicone oil (hereinafter also simply referred to as a "second silicone oil") is represented by the following formula (2),

[Chemical Formula 4]

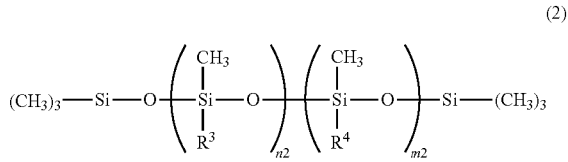

wherein: $R^3$ is an alkyl group having 6 or more carbon atoms; $R^4$ is selected from the group consisting of an aralkyl group, a phenyl group, and a mercaptoalkyl group; n2 is a positive integer; and m2 is 0 or a positive integer.

$R^3$ in the formula (2) is an alkyl group having 6 or more carbon atoms. The upper limit of the number of carbon atoms is not limited, but it is usually 14. That is, the number of carbon atoms of $R^3$ is preferably 6 to 14. Examples of the alkyl group having 6 or more carbon atoms in $R^3$ include a hexyl group (including various hexyl groups such as a n-hexyl group), an octyl group, a nonyl group, a decyl group, an undecyl group, and a dodecyl group.

The aralkyl group and the mercaptoalkyl group in $R^4$ are the same as the respective groups in $R^2$ described above. When the first silicone oil and the second silicone oil are used in combination, $R^2$ and $R^4$ may be the same group or different groups.

Furthermore, at least one of hydrogen atoms constituting the alkyl group as $R^3$, and the aralkyl group, phenyl group, and mercaptoalkyl group as $R^4$ may be substituted with a halogen atom. Examples of the halogen atom include a fluorine atom and a chlorine atom.

When the silicone oil contains the second silicone oil, the silicone oil has tackiness to allow a coated film which is hard to flow from the applied surface of the mold to be formed. Therefore, the silicone oil containing the second silicone oil is suitable for casting a molten metal at a high feed flow rate.

When the silicone oil contains the second silicone oil, the ratio of the second silicone oil to the total of the silicone oil is preferably 70% by mass or less (may be 0% by mass). This makes it possible to prevent the solidification of the mold release agent composition to suppress the baking thereof. The ratio of the second silicone oil to the total of the silicone oil is preferably 55% by mass or less, more preferably 35% by mass or less, and still more preferably 25% by mass or less.

Although n2 in the formula (2) is not limited, for example, $1 \leq n2 \leq 3000$ can be set. Furthermore, $1 \leq n2 \leq 500$ can be set. Although m2 in the formula (2) is not limited, for example, $0 \leq m2 \leq 3000$ can be set. Furthermore, $1 \leq m2 \leq 500$ can be set. Although the correlation between n2 and m2 is not particularly limited, for example, $10 \leq (n2+m2) \leq 3000$ can be set. Furthermore, $10 \leq (n2+m2) \leq 500$ can be set.

The silicone oil may contain a third silicone oil in addition to the first silicone oil and the second silicone oil.

Examples of the third silicone oil include a silicone oil referred to as a non-modified straight oil. Specific examples thereof include a dimethyl silicone oil (a polysiloxane having a side chain of a methyl group), a methylphenyl silicone oil (a polysiloxane having a side chain of a methyl group and phenyl group), a methyl hydrogen silicone oil (a polysiloxane having a side chain of a methyl group and hydrogen atom). These may be used alone or in combination of two or more.

When the silicone oil contains the third silicone oil, the ratio of the third silicone oil to the total of the silicone oil is preferably 10% by mass or less, more preferably 7% by mass or less, and particularly preferably 5% by mass or less.

When the total amount of the mold release agent composition for use in casting is 100% by mass, the silicone oil is usually contained in an amount of 10% by mass or more, and preferably 50% by mass or less. This range makes it possible to particularly effectively increase the Leidenfrost temperature of the mold release agent composition for use in casting. That is, specifically, the Leidenfrost temperature can be set to 350° C. or higher. Furthermore, the ratio is more preferably 15 to 50% by mass, and particularly preferably 20 to 40% by mass.

The mold release agent composition for use in casting contains a solvent in addition to the silicone oil.

The above-mentioned solvent is a component which exhibits a function of diluting a component such as the silicone oil and maintaining a viscosity allowing the application amount to be stabilized, in the mold release agent composition for use in casting.

Examples of the solvent include a paraffin and an olefin. These may be used alone or in combination of two or more.

The blending ratio of the solvent is not particularly limited, but it is usually at least 30% by mass or more, and preferably 50% by mass or more, when the total amount of the mold release agent composition for use in casting is taken as 100% by mass. Furthermore, the ratio is more preferably 50 to 90% by mass, and particularly preferably 55 to 80% by mass.

Furthermore, the mold release agent composition for use in casting may contain at least one of a mineral oil and a synthetic oil, in addition to the silicone oil and the solvent.

The mineral oil and the synthetic oil (hereinafter also collectively referred to as a "non-silicone oil") function as a component promoting the uniformization of a coated film formed on the surface of a mold.

Of these, the mineral oil is an oil obtained by distilling and refining petroleum, and the kind thereof is not particularly limited. Examples of the mineral oil include a paraffinic mineral oil, a naphthenic mineral oil, and an aromatic mineral oil. These may be used alone or in combination of two or more.

Examples of the synthetic oil include synthetic hydrocarbon oils such as a polyolefin oil, an alkyl aromatic oil, and a cycloalkane oil; ester synthetic oils such as a monoester oil, a diester oil, a polyol ester oil, and a phosphoric ester; and polyether-based synthetic oils such as a polyglycol oil and a phenyl ether oil. These may be used alone or in combination of two or more.

The kinematic viscosity of the non-silicone oil is not particularly limited, but for example, a non-silicone oil can be used, which has a kinematic viscosity at 40° C. (kinematic viscosity measured by a Cannon-Fenske viscometer according to JIS K 2283) of 20 mm$^2$/s or more. Among these, a non-silicone oil having a kinematic viscosity of 40 to 500 mm$^2$/s is preferable; a non-silicone oil having a kinematic viscosity of 100 to 400 mm$^2$/s is more preferable; and a non-silicone oil having a kinematic viscosity of 150 to 350 mm$^2$/s is particularly preferable.

The blending ratio of the non-silicone oil is not particularly limited, but it is usually 1% by mass or more, and preferably 10% by mass or less when the total amount of the mold release agent composition for use in casting is taken as 100% by mass. Furthermore, the ratio is more preferably 1 to 7% by mass, and particularly preferably 1 to 5% by mass.

The mold release agent composition for use in casting of the present invention may contain other components in addition to the silicone oil, the solvent, and the non-silicone oil. Examples of the other components include a radical capture agent, a radical capture auxiliary agent, an extreme-pressure additive, a surfactant, a defoaming agent, a flame retardant, and an anticorrosive agent. These may be used alone or in combination of two or more.

The radical capture agent is a component capable of suppressing the radical polymerization of components constituting a silicone oil or a non-silicone oil, and decomposed products thereof. That is, the mold release agent composition for use in casting contains the radical capture agent, which makes it possible to effectively maintain the oily property of the mold release agent composition for use in casting.

Examples of the radical capture agent include a phenol-based antioxidant, an amine-based antioxidant, a sulfur-based antioxidant, a phosphorus-based antioxidant, a hydrazine-based antioxidant, and an amide-based antioxidant. Among these, the phenol-based antioxidant or the like is preferable. These may be used alone or in combination of two or more.

The blending ratio of the radical capture agent is not particularly limited, but from the viewpoint of securing the oily property of the coated film and from the viewpoint of preventing precipitation at low temperature, the blending ratio of the radical capture agent is usually at least 0.01% by mass or more, and preferably 0.1% by mass or more when the total amount of the mold release agent composition for use in casting is taken as 100% by mass. Furthermore, this ratio is more preferably 0.2 to 8% by mass, and particularly preferably 0.3 to 5% by mass.

When the total amount of the silicone oil is taken as 100 parts by mass, the ratio of the radical capture agent is preferably 0.5 to 10 parts by mass, more preferably 1 to 5 parts by mass, and particularly preferably 1 to 3 parts by mass.

The radical capture auxiliary agent is an organometallic compound capable of assisting the function of the radical capture agent. Specific examples thereof include zinc dialkyl dithiophosphate, molybdenum dialkyl dithiophosphate, molybdenum dialkyldicarbamate, and dialkylamine molybdate. Among these, zinc dialkyl dithiophosphate, molybdenum dialkyl dithiophosphate, and molybdenum dialkyl dicarbamate or the like are preferable. These may be used alone or in combination of two or more.

The blending ratio of the radical capture auxiliary agent is not particularly limited, but the blending ratio is usually at least 0.01% by mass or more, and preferably 0.1% by mass or more when the total amount of the mold release agent composition for use in casting is taken as 100% by mass. Furthermore, this ratio is more preferably 0.2 to 8% by mass, and particularly preferably 0.3 to 5% by mass.

When the total amount of the silicone oil is taken as 100 parts by mass, the amount of the radical capture auxiliary agent is preferably 0.5 to 10 parts by mass, more preferably 1 to 5 parts by mass, and particularly preferably 1 to 3 parts by mass.

Furthermore, when the total amount of the radical capture auxiliary agent is taken as 100 parts by mass, the amount of the radical capture auxiliary agent is preferably 30 to 200 parts by mass, more preferably 50 to 150 parts by mass, and particularly preferably 70 to 130 parts by mass.

The various performances of the mold release agent composition for use in casting are not particularly limited, but the kinematic viscosity at 40° C. is 1 to 30 mm$^2$/s (kinematic viscosity measured by a Cannon-Fenske viscometer according to JIS K 2283). This kinematic viscosity is more preferably 1 to 20 mm$^2$/s, and still more preferably 1 to 10 mm$^2$/s.

"Silicone oil S1-C3": a first silicone oil represented by the formula (1); $R^1$ is an alkyl group having 3 carbon atoms; $R^2$ is an aralkyl group (α-methylstyrene group); and m1 is a positive integer.

"Silicone oil S1-C4": a first silicone oil represented by the formula (1); $R^1$ is an alkyl group having 4 carbon atoms; $R^2$ is an aralkyl group (α-methylstyrene group); and m1 is a positive integer.

"Silicone oil S2-C6": a second silicone oil represented by the formula (2); $R^3$ is an alkyl group having 6 carbon atoms; $R^4$ is an aralkyl group (α-methylstyrene group); and m2 is a positive integer.

"Silicone oil S2-C10": a second silicone oil represented by the formula (2); $R^3$ is an alkyl group having 10 carbon atoms; $R^4$ is an aralkyl group (α-methylstyrene group); and m2 is a positive integer.

"Silicone oil S2-C12": a second silicone oil represented by the formula (2); R3 is an alkyl group having 12 carbon atoms; $R^4$ is an aralkyl group (α-methylstyrene group); and m2 is a positive integer.

"Mineral oil": the mineral oil has a kinematic viscosity at 40° C. according to JIS K 2283 of 100 to 300 mm$^2$/s.

"Radical capture agent": a phenol-based antioxidant

"Radical capture auxiliary agent": molybdenum dialkyldithiophosphate

"Solvent": The solvent is a paraffin. The Leidenfrost temperature of the paraffin alone is 240° C.

TABLE 1

| | | | Examples | | | | | | | | | Comparative Examples | | |
|---|---|---|---|---|---|---|---|---|---|---|---|---|---|---|
| | | | 1 | 2 | 3 | 4 | 5 | 6 | 7 | 8 | 9 | 1 | 2 | 3 |
| Silicone oil | First | S1-C1 | — | — | — | 10 | 10 | 10 | — | — | — | — | — | — |
| | | S1-C3 | — | — | — | — | — | — | 10 | 10 | 10 | — | — | — |
| | | S1-C4 | 30 | 20 | 10 | — | — | — | — | — | — | — | 5 | 7.5 |
| | Second | S2-C6 | — | 10 | 20 | 20 | — | — | 20 | — | — | 30 | 25 | 22.5 |
| | | S2-C10 | — | — | — | — | 20 | — | — | 20 | — | — | — | — |
| | | S2-C12 | — | — | — | — | — | 20 | — | — | 20 | — | — | — |
| Mineral oil | | | | | | | 5 | | | | | | 5 | |
| Radical capture agent | | | | | | | 0.5 | | | | | | 0.5 | |
| Radical capture auxiliary agent | | | | | | | 0.5 | | | | | | 0.5 | |
| Solvent | | | | | | | 64 | | | | | | 64 | |
| Total | | | | | | | 100 | | | | | | 100 | |
| State of Coated film | | | Oily | Semi-oily | Semi-oily | Oily | Oily | Oily | Oily | Oily | Oily | Solid | Solid | Solid |
| Mold release resistance (kg) | | | 8 | 10 | 12 | 7 | 11 | 12 | 9 | 12 | 13 | >20 | >20 | >20 |
| Lubricity (Number of slidings) | | | >20 | >20 | 15 | >20 | >20 | >20 | >20 | >20 | >20 | 1 | 1 | 3 |

EXAMPLES

Hereinafter, the present invention will be specifically described with reference to Examples.

[1] Preparation of Mold Release Agent Composition for Use in Casting

Various components were mixed at ratios shown in Table 1 to obtain mold release agent compositions for use in casting of Examples 1 to 9 and mold release agent compositions for use in casting of Comparative Examples 1 to 3. The various components used in the preparation of the mold release agent compositions for use in casting are as follows.

"Silicone oil S1-C1": a first silicone oil represented by the formula (1); $R^1$ is an alkyl group having 1 carbon atom; $R^2$ is an aralkyl group (α-methylstyrene group); and m1 is a positive integer.

[2] Evaluation of State of Coated Film

Using the mold release agent compositions for use in casting of Examples 1 to 9 and Comparative Examples 1 to 3 prepared in the above [1], the state of a coated film provided by each of the mold release agent compositions for use in casting applied on the surface of a mold material by the following method (see FIG. 1) was evaluated.

(1) A metal material 1 (SPCC-SB steel plate specified in JIS G 3141, surface mirror finishing material of cold rolled steel plate, 100 mm×100 mm×2 mm) was heated and held at 400° C.

(2) Approximately 0.4 cc of each of the mold release agent compositions for use in casting 3 of Examples 1 to 9 and Comparative Examples 1 to 3 was spray-applied on the metal material 1 (applying time: 0.5 seconds, distance between the metal material 1 and a spray: 150 mm), and held for 20 seconds to form an applied surface 2 before contact with molten metal {see FIG. 1(*a*)}.

(3) A cylindrical jig 4 (inner diameter: 75 mm) was placed on the metal material 1 so as to cover the applied surface 2.
(4) An aluminum molten metal (100 cc) of 680° C. was charged into the cylindrical jig 4 {see FIG. 1(*b*)}.
(5) After 40 seconds from the charging of the molten metal, the cylindrical jig 4 and an aluminum solidified product 5 were removed to expose an applied surface 2' after contact with molten metal {see FIG. 1(*c*)}.
(6) The elemental analysis of the applied surface 2 and applied surface 2' was performed for Si using an X-ray analysis microscope (model "XGT-5000" manufactured by HORIBA, Ltd.).

Figure 2:
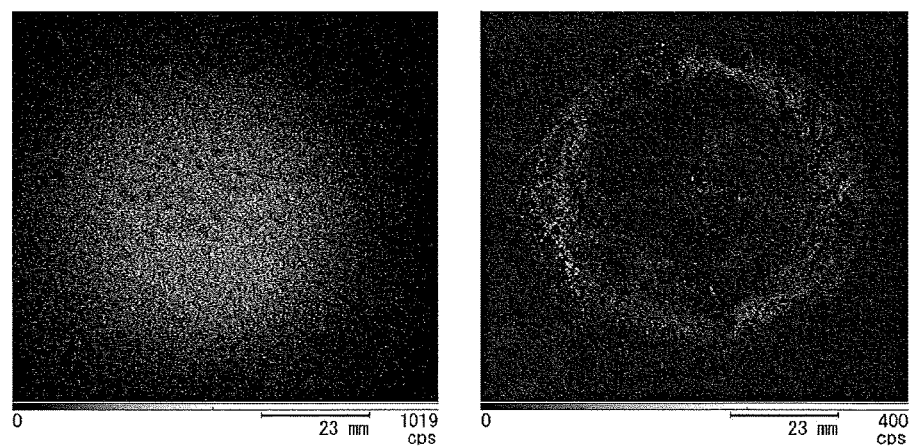
FIG. 2 is a chart in which flow traces are observed.

As a result, in charts obtained for Example 1 and Example 2, flow traces were observed (see FIG. 2, the left is a chart before contact with molten metal, and the right is a chart after contact with molten metal). That is, in the chart before contact with molten metal in Example 1 and Example 2, a uniform circular Si distribution was observed on the applied surface, but in the chart after contact with molten metal, a ring-like Si distribution was observed on the applied surface 2'. This change is thought to be a trace of the coated film being moved from the center to the outer periphery by charging the aluminum molten metal (that is, a flow trace). From this, it can be said that the mold release agent compositions for use in casting of Examples 1 and 2 are in an oily state. The mold release agent compositions for use in casting were confirmed to have high fluidity maintained even at high temperature (400 to 680° C.).

In a chart obtained for Example 3, flow traces were observed, but it was less than that in Example 1 and Example 2. Furthermore, no flow traces were observed in Comparative Examples 1 to 3. That is, in the chart before contact with molten metal in Example 3, a uniform circular Si distribution was observed on the applied surface. In the chart after contact molten metal, a ring-like Si distribution was observed on the applied surface 2', and had a lower concentration than that of the ring shape observed in the chart after contact with molten metal in Example 1 and Example 2. That is, this is thought to be because the flow traces are observed, but the coated film formed on the applied surface 2 becomes semi-oily, and the adhesion of the coated film to the metal material 1 is improved as compared with Examples 1 and 2. The movement of the coated film is not notable as compared with Examples 1 and 2. From this, it can be said that the mold release agent composition for use in casting of Example 3 is semi-oily.

Figure 3:
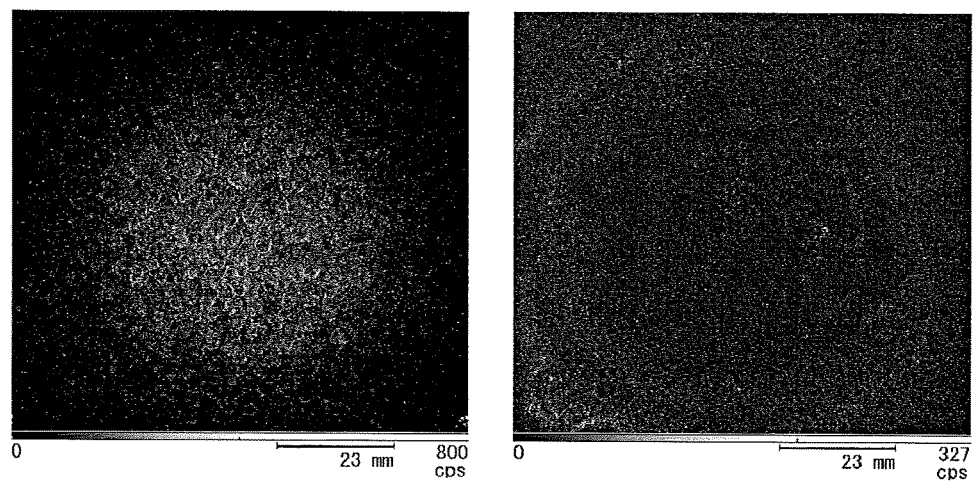
FIG. 3 is a chart in which flow traces are not observed.

On the other hand, in charts obtained for Comparative Examples 1 to 3, a uniform circular Si distribution was observed on the applied surface, but in the chart after contact with molten metal, a ring-shaped Si distribution was not observed on the applied surface 2' (see FIG. 3, the left is a chart before contact with molten metal, the right is a chart after contact with molten metal). That is, no flow traces of the coated film were observed. This is thought to be because the mold release agent compositions for use in casting of Comparative Examples 1 to 3 are solidified. From this, it can be said that the mold release agent compositions for use in casting of Comparative Examples 1 to 3 are solids.

In FIGS. 2 and 3, the reason why the detection intensity of the applied surface 2' is lower than that of the applied surface 2 is that a part of the coated film adheres to the aluminum solidified product, and is removed from the applied surface 2'.

[3] Evaluation of Mold Release Resistance

Figure 4:
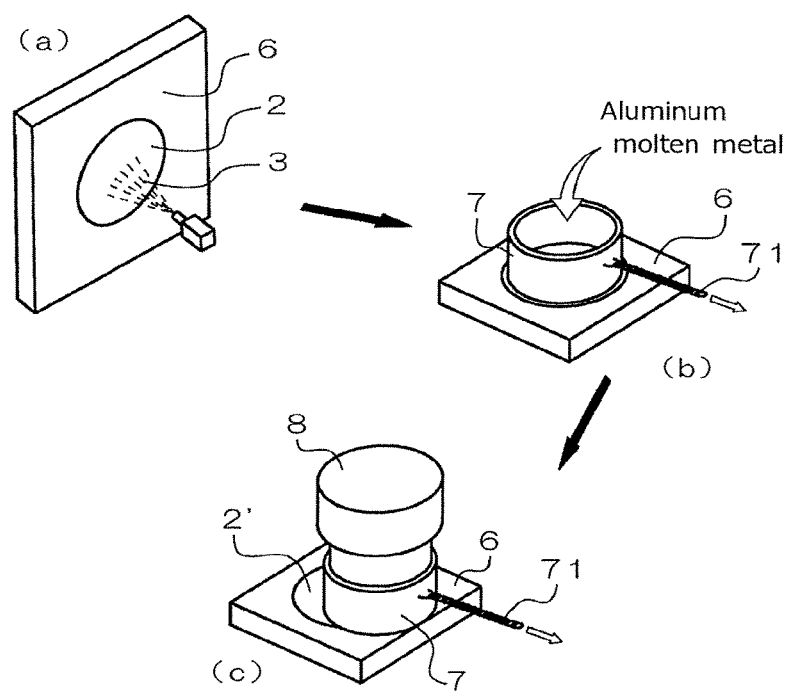
FIG. 4 is an explanatory diagram illustrating a method for evaluating mold release resistance in Examples.

Using the mold release agent compositions for use in casting of Examples 1 to 9 and Comparative Examples 1 to 3 prepared in the above [1], the mold release resistances of the mold release agent compositions for use in casting applied on the surface of the mold material by the following method (see FIG. 4) were evaluated.
(1) A metal material 6 (SKD 61 steel plate specified in JIS G 4404, alloy tool steel material, 200 mm×200 mm×30 mm) was heated and held at 400° C.
(2) Approximately 0.4 cc of each of the mold release agent compositions for use in casting 3 of Examples 1 to 9 and Comparative Examples 1 to 3 was spray-applied on the metal material 6 (applying time: 0.5 seconds, distance between the metal material 1 and a spray: 150 mm), and held for 20 seconds to form an applied surface 2 before contact with molten metal {see FIG. 4(*a*)}.
(3) A cylindrical jig 7 (inner diameter: 75 mm) attached with a chain 71 for peeling off was placed on the metal material 6 so as to cover the applied surface 2.
(4) An aluminum molten metal (100 cc) of 680° C. was charged into the cylindrical jig 7 {see FIG. 4(*b*)}.
(5) After 40 seconds from the charging of the molten metal, a weight 8 (9 kg) was placed on an aluminum solidified product. Thereafter, after 20 seconds, the mold release resistance when the chain 71 was pulled was measured {see FIG. 4(*c*)}.

As a result, in Examples 1 to 9, sticking did not occur, and the mold could be released without problems with a pulling load of 7 to 13 kg. On the other hand, in Comparative Examples 1 to 3, baking occurred, and the metal material 6 and the aluminum solidified product were welded together, so that the mold could not be released even with a pulling load of 20 kg.

[4] Evaluation of Lubricity (Number of Slidings)

Figure 5:
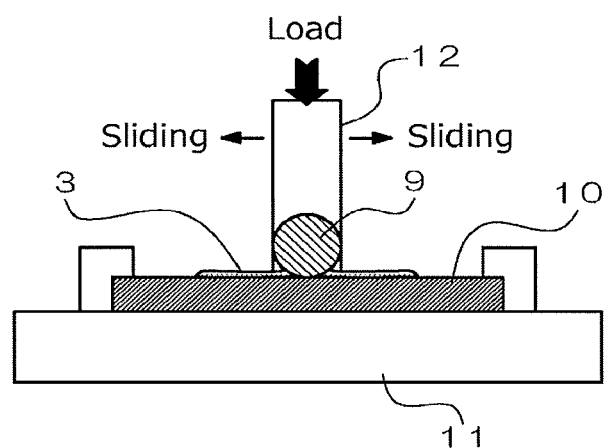
FIG. 5 is an explanatory diagram illustrating a method for evaluating lubricity in Examples.

Using the mold release agent compositions for use in casting of Examples 1 to 9 and Comparative Examples 1 to 3 prepared in the above [1], the lubricities of the mold release agent compositions for use in casting were evaluated by the following method (see FIG. 5).
(1) A metal material 10 (SKD 61 steel plate specified in JIS G 4404, alloy tool steel material, 30 mm×100 mm×2 mm) was heated and held at 400° C. on a heater 11.
(2) Approximately 0.2 cc of each of the mold release agent compositions for use in casting 3 of Examples 1 to 9 and Comparative Examples 1 to 3 was dropped on the metal material 10.
(3) A steel ball 9 (manufactured by SUJ-2, $\varphi^3/_{16}$ inches) was placed on the metal material 10 via each of the mold release agent compositions for use in casting 3, and a load of 4 kg was attached to the steel ball 9 via a steel ball fixed column 12.
(4) In the state of the metal material 10 at a temperature of 200° C., the steel ball 9 was slid together with the steel ball fixed column 12 on the surface of the metal material 10 via each of the mold release agent compositions for use in casting 3. The friction coefficient ($\mu$) during sliding was measured using a surface property measuring machine (manufactured by Shinto Scientific Co., Ltd., model "HEIDON TRIBOGEAR TYPE: 38"). The sliding speed during measuring was set to 4 mm/sec, and the sliding distance was set to 25 mm.

Figure 7:
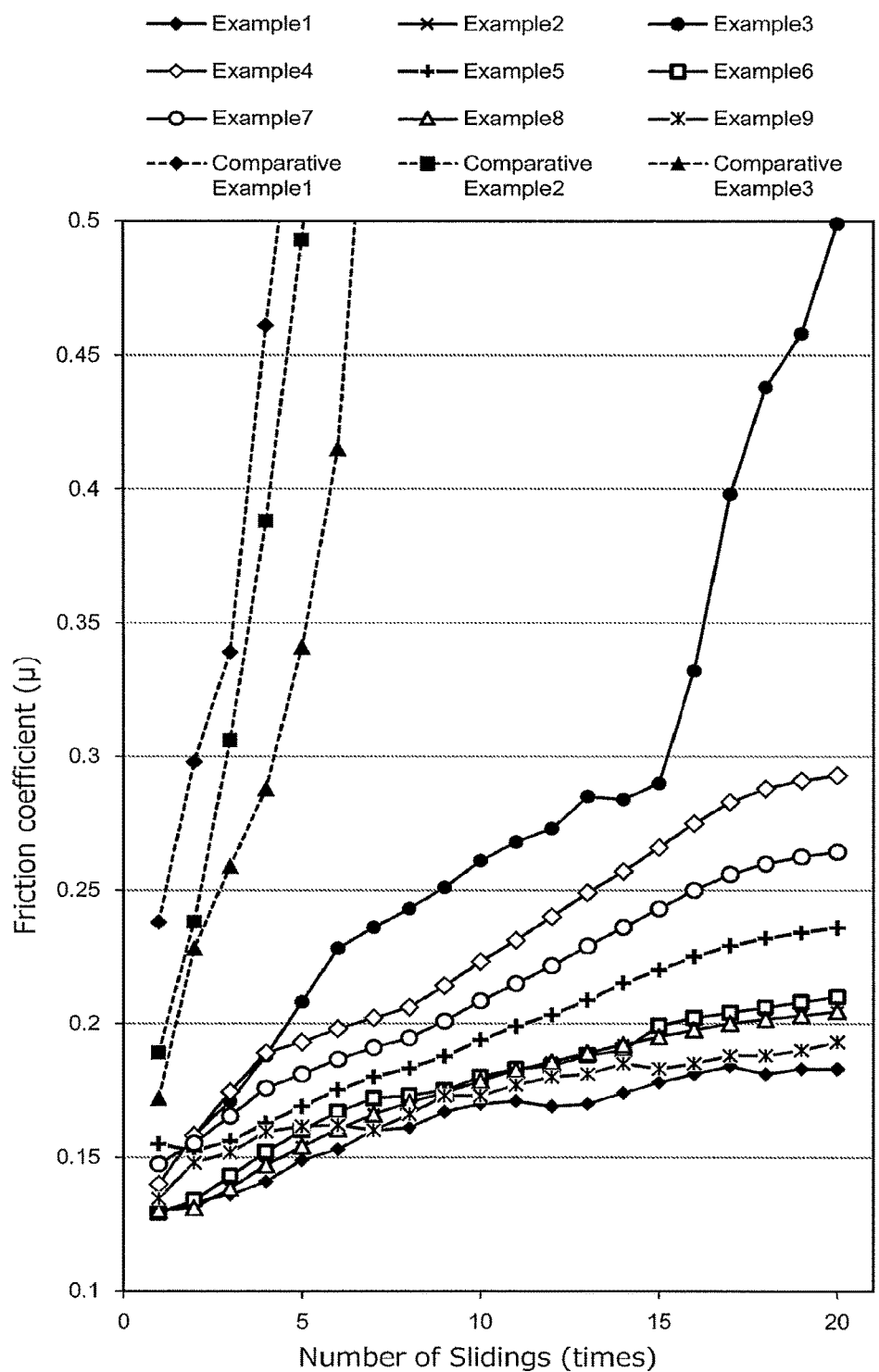
FIG. 7 is a graph showing the evaluation results of lubricity in Examples.

The results are shown in FIG. 7.

As a result, in Comparative Examples 1 to 3, the friction coefficient ($\mu$) was about 0.2 from the first sliding, but the friction coefficient was sharply increased from the second sliding. On the other hand, in Examples 1 to 9, the friction coefficient ($\mu$) was 0.4 or less until the first to 15th slidings, which could provide stable sliding. Particularly, the mold release agent compositions for use in casting other than Example 3 made it possible to maintain the coefficient of friction (μ) of 0.3 or less during 20 or more slidings. The coefficient of friction of the mold release agent composition for use in casting of Example 3 was gently increased during the first to 15th slidings. The increase of the friction coefficient was started after 16th sliding, and the friction coefficient finally exceeded 0.4.

This result is surprisingly contrary to the result that a silicone oil having a longer alkyl chain generally has better lubricity. That is, a composition containing a silicone oil having a short alkyl chain exhibited better slidability. This result is presumed to be because, in Comparative Examples 1 to 3 in which the oil state cannot be maintained under high temperature, the sufficient lubricity cannot be obtained by the thermal deterioration of the component of the mold release agent.

[5] Evaluation of Leidenfrost Temperature

Compositions of Reference Examples 1 to 6 having formulations shown in the following Table 2 were prepared, and the Leidenfrost temperature was evaluated by the following method (see FIG. 6).

Figure 6:
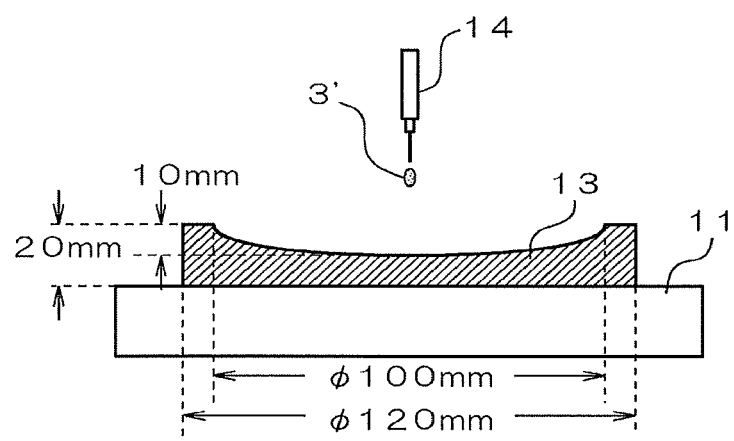
FIG. 6 is an explanatory diagram illustrating a method for evaluating a Leidenfrost temperature in Examples.

That is, a recessed metal material 12 shown in FIG. 6 was prepared. The temperature of the metal material 12 was varied, and each of compositions 3' of Reference Examples 1 to 6 shown in Table 2 was dropped from a syringe 13. The temperature at which the Leidenfrost phenomenon occurred was measured. The results are shown in Table 2. Various components used for evaluating the Leidenfrost temperatures are as follows.

"Silicone oil S1-C1a" is a first silicone oil represented by the formula (1); $R^1$ is an alkyl group having 1 carbon atom; $R^2$ is an aralkyl group (α-methylstyrene group); m1 is a positive integer; and a viscosity is 100 cSt/25° C.

"Silicone oil S1-C1b": a first silicone oil represented by the formula (1); $R^1$ is an alkyl group having 1 carbon atom; $R^2$ is an aralkyl group (α-methylstyrene group); m1 is a positive integer; and a viscosity is 1000 cSt/25° C.

TABLE 2

|  | Reference Examples | | | | | |
| --- | --- | --- | --- | --- | --- | --- |
|  | 1 | 2 | 3 | 4 | 5 | 6 |
| Silicone oil S1-C1 (a) 100 cSt/25° C. | 10 | 15 | 20 | — | — | — |
| Silicone oil S1-C1 (b) 1000 cSt/25° C. | — | — | — | 10 | 15 | 20 |
| Solvent | 90 | 85 | 80 | 90 | 85 | 80 |
| Total | 100 | 100 | 100 | 100 | 100 | 100 |
| Leidenfrost temperature (° C.) | 368 | 382 | 394 | 372 | 390 | 406 |

From the results in Table 2, it was confirmed that a temperature at which the Leidenfrost phenomenon occurs (Leidenfrost temperature) is gradually increased by increasing the blending amount of the first silicone oil.

It should be noted that the present invention is not limited to the above-described Examples, and various modifications or changes are possible within the scope of claims of the present invention.

INDUSTRIAL APPLICABILITY

The mold release agent composition for use in casting of the present invention is widely used as a mold release agent for various castings. Examples of the casting method include a mold casting method, a low pressure casting method, a squeeze casting method, a nonporous die casting method, a vacuum die casting method, a thixomolding method, and a combination of these methods. The mold release agent composition for use in casting can be used for casting various metals, but it is particularly suitable for light metals and light metal alloys. Specific examples thereof include aluminum, magnesium, zinc, and alloys of these metals.

REFERENCE SIGNS LIST 1 metal material
2 applied surface of mold release agent composition for use in casting (before contact with molten metal)
2' applied surface of mold release agent composition for use in casting (after contact with molten metal)
3 mold release agent composition for use in casting
3' composition of Reference Example
4 cylindrical jig
5 aluminum solidified product
6 metal material
7 cylindrical jig
71 chain
8 weight
9 steel ball
10 metal material
11 heater
12 steel ball fixing column
13 metal material
14 syringe

The invention claimed is:

1. A mold release agent composition, comprising:
a silicone oil; and
a solvent,
wherein:
the silicone oil comprises both a first silicone oil of formula (1) and a second silicone oil represented by formula (2); and
an amount of the first silicone oil is 30% by mass or more and an amount of the second silicone oil is 70% by mass or less, with respect to a total amount of the silicone oil,

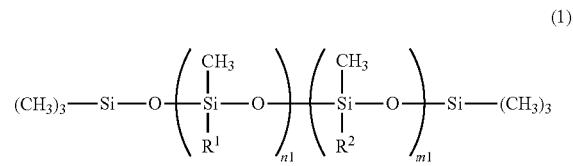

(1)

wherein:
$R^1$ is an alkyl group comprising 1 to 4 carbon atoms;
$R^2$ is an aralkyl group in which an aryl group has an alkyl group as a substituent, where the aryl group has 6 to 14 carbon atoms and the alkyl group has 1 to 12 carbon atoms;
n1 is a positive integer; and
m1 is a positive integer,

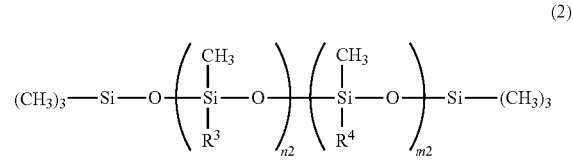

(2)

wherein:
- $R^3$ is an alkyl group comprising 6 or more carbon atoms;
- $R^4$ is an aralkyl group in which an aryl group has an alkyl group as a substituent, where the aryl group has 6 to 14 carbon atoms and the alkyl group has 1 to 12 carbon atoms;
- n2 is a positive integer; and
- m2 is 0 or a positive integer.

2. The mold release agent composition according to claim 1, wherein an amount of the silicone oil is 15% by mass or more with respect to a total amount of the silicon oil and the solvent.

3. The mold release agent composition according to claim 1, wherein an amount of the solvent is 55% by mass or more with respect to a total amount of the mold release agent composition.

4. The mold release agent composition according to claim 1, further comprising:
a mineral oil and/or a synthetic oil.

5. The mold release agent composition according to claim 1, further comprising:
a radical capture agent.

6. The mold release agent composition according to claim 5, wherein when the total amount of the silicone oil is taken as 100 parts by mass, a blended amount of the radical capture agent is 1 part by mass or more.

7. The mold release agent composition according to claim 5, further comprising:
an organometallic compound as an auxiliary agent for the radical capture agent.

8. The mold release agent composition according to claim 7, wherein the aralkyl group is an α-methylstyrene group.

9. The mold release agent composition according to claim 1, wherein:
- n1 satisfies the expression of $1 \leq n1 \leq 3000$;
- m1 satisfies the expression of $1 \leq m1 \leq 3000$; and
- the expression of $10 \leq (n1+m1) \leq 3000$ is satisfied.

10. The mold release agent composition according to claim 2, wherein an amount of the solvent is 55% by mass or more with respect to a total amount of the mold release agent composition.

11. The mold release agent composition according to claim 10, further comprising:
a mineral oil and/or a synthetic oil.

12. The mold release agent composition according to claim 11, further comprising:
a radical capture agent.

13. The mold release agent composition according to claim 12, wherein when the total amount of the silicone oil is taken as 100 parts by mass, a blended amount of the radical capture agent is 1 part by mass or more.

14. The mold release agent composition according to claim 12, further comprising:
an organometallic compound as an auxiliary agent for the radical capture agent.

15. The mold release agent composition according to claim 14, wherein the aralkyl group is an α-methylstyrene group.

16. The mold release agent composition according to claim 12, wherein:
- n1 satisfies the expression of $1 \leq n1 \leq 3000$;
- m1 satisfies the expression of $1 \leq m1 \leq 3000$; and
- the expression of $10 \leq (n1+m1) \leq 3000$ is satisfied.

* * * * *